United States Patent [19]

Grode

[11] 4,455,299

[45] Jun. 19, 1984

[54] STORAGE OF BLOOD PLATELETS

[75] Inventor: Gerald A. Grode, Grayslake, Ill.

[73] Assignee: Baxter Travenol Laboratories, Inc., Deerfield, Ill.

[21] Appl. No.: 323,224

[22] Filed: Nov. 20, 1981

[51] Int. Cl.³ .................... A61K 35/14; A01N 1/02
[52] U.S. Cl. .................................. 424/101; 435/2; 206/0.5; 206/439
[58] Field of Search ........................... 424/101; 435/2

[56] References Cited

U.S. PATENT DOCUMENTS

| | | | |
|---|---|---|---|
| 3,276,589 | 10/1966 | Jankay | 210/175 |
| 3,441,479 | 4/1969 | Jankay | 195/1.8 |
| 3,729,947 | 5/1973 | Higuchi | 62/60 |
| 3,735,005 | 5/1973 | Shio et al. | 424/101 |
| 4,082,509 | 4/1978 | Talcott | 21/58 |
| 4,132,594 | 1/1979 | Bank et al. | 195/1.8 |
| 4,228,032 | 10/1980 | Talcott | 252/400 R |

OTHER PUBLICATIONS

Handin et al.–Chem. Abst., vol. 88, (1978), p. 19740e.
Hulsman et al.–Chem. Abst., vol. 71, (1969), p. 89324v.
Rock et al., "Transfusion" 21(2): 167–177, (1981).
Murphy et al., "Blood" 46: (2): 209–218, (1975).
Holme et al., "Blood" 52: (2)425–425–435, (1978).
Rock et al., "Transfusion" 16(6): 571–579, (1976).
Rosenstein et al., "Am. J. Clin. Path." 73(3): 397–399, (1980).
Steele et al., "Circulation" 55(4): 660–662, (1977).
"Transfusion" 13(5): 351, (1973).

*Primary Examiner*—Sam Rosen
*Attorney, Agent, or Firm*—Max D. Hensley; Paul C. Flattery

[57] ABSTRACT

Blood platelet pH is maintained between 6.0 and 7.6 for up to at least five days in relatively low gas permeability containers, e.g., standard polyvinyl chloride containers, by exposing the container to an atmosphere having an oxygen content greater than about 21%.

13 Claims, 2 Drawing Figures

STORAGE OF BLOOD PLATELETS

BACKGROUND OF THE INVENTION

The present invention relates, in general, to the storage of blood and blood components. More particularly, it is directed to improvements in the storage of blood platelets for enhancing in vivo viability by storing the platelets in gas permeable containers in an oxygen-enriched atmosphere.

Because of the limited supply of whole blood available from donors, it has become the practice to fractionate whole blood into various of its component parts, e.g., plasma, platelets and erythrocytes. In this manner, patients in need of treatment by a particular blood component will be given only that component rather than whole blood. Thus, the limited supply of whole blood can be more efficiently used in the treatment of a larger number of people.

One factor, however, which limits the benefits of blood fractionation is the limited storage time possible for many blood components. If stored too long, a substantial reduction in the in vivo activity occurs, and thus the effectiveness of the treatment is compromised. Blood platelets, in particular, which assist in blood clotting, have been found to have a very limited storage life, typically less than about seventy-two hours. On the other hand, the medical usage of blood platelets, such as in the treatment of thrombocytopenia, has been on the increase. Accordingly, there is a continuing desire to improve and lengthen the storage time possible for blood platelets.

Although a number of elements have been identified as affecting the viability of platelets during storage, pH has been recognized as one of the best correlatives of in vivo platelet viability. In particular, in a paper entitled "Platelet Storage at 22° C.: Role of Gas Transport Across Plastic Containers in Maintenance of Viability", by Murphy and Gardner, in Blood, 46:209, 1975, a pH range of generally between 6 and 7.6 was indicated as being preferred for storage at 22° C. (72° F.). Beyond this range of pH, a disc-to-sphere morphology change occurs which results in marked loss of platelet in vivo activity. The authors report that such deleterious pH changes, particularly into the acidic range, can be delayed if platelets are stored in containers constructed of a material such as polyethylene which is more permeable to $O_2$ and $CO_2$ than conventional containers made of 0.015 inch thick polyvinyl chloride. Polyethylene containers were disclosed in exhibit an $O_2$ transport rate approximately twice as rapid as that across polyvinyl chloride. The authors suggest, however, that the improved platelet activities obtained in polyethylene containers also could be achieved by the use of thin polyvinyl chloride, (0.008 inches in thickness) since the rate of gas transport across plastic is inversely proportional in a linear fashion to the plastic's thickness. In addition, the authors disclose that storing platelets in polyethylene bags under a 10% $CO_2$-in-air atmosphere further improves the viability of the stored platelets.

While platelet viability is enhanced by the use of thin-walled polyvinyl chloride containers having enhanced $O_2$ and $CO_2$ permeability, such containers are not without disadvantages. Quality control during the manufacture of the bags becomes more critical than ever because of the greater risk that defects in the thin film may create an opening for microbial entry into the bag. The bags must be handled with greater care during use for the same reason. Further, it would be desirable if conventional bags of low gas permeability could continue in use.

OBJECTS OF THE INVENTION

It is an object of this invention to provide a system for improving platelet viability without the risks attendant the use of certain thin-walled containers.

It is another object to improve the composition of atmospheres under which platelets are stored so as to prolong the storage life of the platlets.

It is a further object of the present invention to provide a method for improving platelet viability without the need for changing or modifying containers of the type currently in use.

These and other objects of the invention will be apparent from consideration of this specification as a whole.

SUMMARY OF THE INVENTION

The foregoing objects are achieved by contacting platelets with an oxygen-enriched atmosphere, i.e., one having an oxygen proportion greater than the 21% oxygen content of air (hereinafter all percentage composition are by volume).

Ordinarily the platelets will be stored as a concentrate in a gas-permeable container made of an organic polymer and the container in turn stored under an atmosphere containing from about 40% to 100% oxygen. Particularly beneficial results are obtained when the enriched oxygen atmosphere is used with platelet containers having low oxygen transfer rates, e.g. on the order of about from 0.050 to 0.010 n moles/cm$^2$-min-cmHg.

A combination for achieving the improved results made possible by this invention includes a substantially gas impermeable plenum enclosing (a) at least a portion of a gas permeable container having platelets stored therein and (b) an atmosphere within the plenum in contact with the container which has a proportion of oxygen greater than about 21%.

Figure 1:
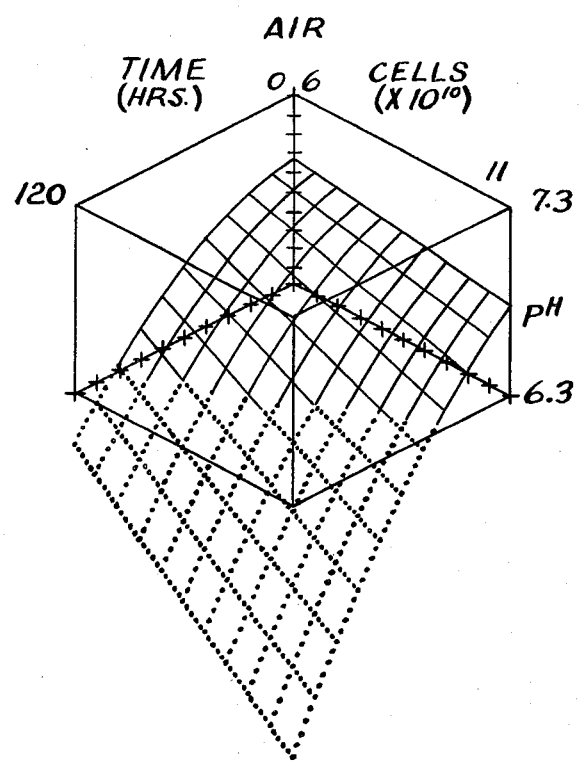

This is to be compared with the results achieved by storage of platelets under air as shown in FIG. 1.

DETAILED DESCRIPTION OF THE INVENTION

The compositions to be contacted with an oxygen-enriched atmosphere are suspensions of platlets in blood plasma or other solutions suitable for the preservation and storage of platelets. Such platelet-containing compositions contain platelets in concentrations higher than are found in blood, and are generally referred to as platlet-rich plasma or, with greater cell populations, platelet concentrates. The methods for preparing such platlet compositions are well known to those skilled in the art. The platelet concentration can range from about 5 to 25×10$^8$ platelets/ml, but will more ordinarily be between 7 and 20×10$^8$ platelets/ml. A concentration of about 12×10$^8$ cells/ml is preferred.

The oxygen-enriched atmosphere is directly or indirectly contacted with the platelets. Direct contact is accomplished by sparging the atmosphere into a platelet suspension or providing the atmosphere in a gas space over the suspension within a gas permeable or impermeable container; in the latter case inlet and outlet ports for gas exchange obviously would be necessary.

Indirect contact is the preferred embodiment. This means that a gas permeable barrier is interposed between the platelets and the enriched oxygen atmosphere. The barrier is ordinarily a film of water insoluble organic polymer such as polyvinyl chloride. The composition of the barrier is not important in the conduct of this invention so long as it is sufficiently sturdy to resist damage in the ordinary laboratory environment, does not leach toxic substances into the stored platelets and has sufficient gas permeability to permit gas exchange as the platelets respire. The barriers with which this invention is particularly concerned are those having an oxygen gas transfer rate of less than about 0.050 n moles/cm$^2$-min-cmHg, more ordinarily less than about 0.040 n moles/cm$^2$-min-cmHg and as low as about 0.010 n moles/cm$^2$-min-cmHg. The barriers are generally formed into unitary containers for the platelet suspension, e.g., bags, tubes and the like. Ordinarily the barriers are constructed as pouches. Conventional polyvinyl chloride pouches commercially available for platelet storage have an oxygen transfer rate of 0.028 n moles/cm$^2$-min-cmHg and a $CO_2$ transfer rate of 0.167 n moles/cm$^2$-min-cmHg. The pouches are comprised of two 0.038 cm layers of polyvinyl chloride film peripherally sealed together to form the container.

In accordance with the present invention, blood platelets are perferably collected directly into a container as described above during the fractionation, which may be carried out employing commercially available apparatus. After platelets are collected into the container, the container is sealed and place in a plenum, chamber, or box for storage at about standard room temperature of 22° C. (72° F.). The container is preferably agitated during storage, as by a rotating shaker, such as the Fenwal elliptical rotating shaker Model No. 4R4050. The shaker is conveniently entirely enclosed by the plenum.

The oxygen-enriched atmosphere will contain a proportion of oxygen greater than the 21% of air, but otherwise the atmosphere need bear no other resemblance to the composition of air. For example, the balance of the atmosphere which is not oxygen may be any relatively biologically inactive gas such as nitrogen or a noble gas. Nitrogen is preferred. The atmosphere should be saturated with water vapor, particularly if it is to be directly contacted with the platelets. The atmosphere may be essentially free of carbon dioxide or may contain as much as the 0.03% normally present in air. However, as much as 2% $CO_2$ may be present at the initial contact of the atmosphere and the container. The proportion of oxygen generally will range from about 25% to 100%, with proportions greater than 40% being more suitable. 80 to 100% is preferred.

It should be understood that the atmosphere which is contacted with the platelets will be in dynamic equilibrium with the respiring cells. Primarily, this means that the initial oxygen concentration will be reduced and carbon dioxide increased as a consequence of cell metabolism. This reduction in oxygen concentration is not of concern so long as the oxygen content of the atmosphere does not fall below about 21%. The carbon dioxide content should not exceed about 5%. Ordinarily the atmosphere over the platelets or that which surrounds the platelet containers will be exchanged approximately once a day.

The invention will be more fully understood by reference to the following example:

EXAMPLE 1

This example demonstrates the improved viability of platelets stored in conventional polyvinyl chloride platelet storage containers under an oxygen-enriched atmosphere. The effect of oxygen in the ambient atmosphere in which the containers were stored is shown for a wide range of cell concentrations. The containers which were tested had platelet contents as described below in Table 1.

TABLE 1

| Container | Total Cell Number ($\times 10^{10}$) | Plasma Volume (ml) | Cells ($\times 10^8$)/ml |
|---|---|---|---|
| 1 | 10.1 | 50.8 | 19.88 |
| 2 | 5.03 | 54.8 | 9.18 |
| 3 | 5.07 | 52.0 | 9.75 |
| 4 | 10.00 | 60.7 | 16.47 |
| 5 | 5.88 | 56.0 | 10.50 |
| 6 | 11.13 | 52.1 | 21.36 |

Platelet rich plasma (PRP) was prepared from CPD anticoagulated whole blood by centrifuging at approximately 4000 Xg for 1 min. Platelet concentrate (PC) was prepared from the PRP by centrifuging at 3300 Xg for 10 minutes. Approximately 54 mils of plasma were left in the PC containers.

The relatively low and high cell concentrations for packs 1, 2, 3 and 6 were made by pooling four units of blood type compatible platelet rich plasma (PRP) and distributing the total volume among 4 packs, ⅛ of the volume to two "low" concentration packs, ⅜ to two "high" concentration packs and the volume brought up by the addition of plasma. The remaining two "medium" concentration packs were prepared from two randomly selected donors.

The containers studied in this example were 12×15 cm polyvinyl chloride bags (280 cm$^2$ surface area) constructed of plastic PL-146, such bags being available commercially from the Fenwal Division of Travenol Laboratories, Deerfield, Ill. PL-146 is 0.015 (0.038 cm) inches in thickness and has a $CO_2$ and oxygen transfer rate, respectively of 59.2 and 7.9 n moles/min-cmHg. The oxygen and $CO_2$ permeability per square centimeter was about 0.028 and 0.167 n moles/cm$^2$-min-cmHg, respectively.

The atmospheres under which the bags were stored were air, 60% oxygen-40% nitrogen and 100% oxygen. Tests in air were conducted by supporting the packs in a standard Fenwal shaker. The tests at high oxygen levels were controlled by building a box around the rack of a Fenwal shaker with a gas inlet at one end and an outlet at the other, each fitted with a piece of tubing and a clamp. Once each 24 hrs (immediately following sampling of the bag contents) the box was purged with the particular atmosphere of interest for 3-5 minutes and then sealed. Agitation was continuous during storage except for the one hour period during sampling and testing. All samples were cultured on blood agar at the end of the study to confirm that no contamination had occured during the extensive sampling.

The pH shift for the contents of each bag was measured daily by withdrawing 0.5 ml of sample, measuring the pH at 37° C. in the anaerobic chamber of a radiometer BM5 MK2 blood microsystem apparatus and adjusting the results to yield a measurement of pH at 22° C.

Figure 2:
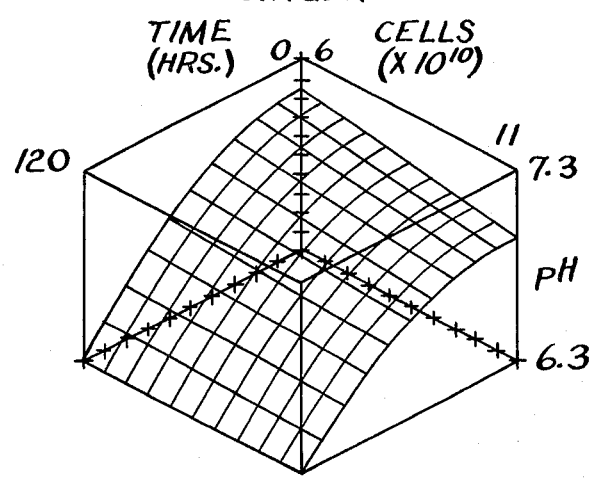
FIG. 2 demonstrates the improved results obtainable by the practice of the invention when storing platelets under an atmosphere having an oxygen concentration of 100%.

The results for air and 100% oxygen are plotted in FIGS. 1 and 2, respectively. The results obtained with the 60-40 mixture of oxygen and nitrogen were similar to those obtained under 100% oxygen; the pH never rose above 7.3 nor fell below 6.0 for the five days of incubation. A comparison of FIGS. 1 and 2 shows that the viability of platelets as measured by the pH stability of PC is improved throughout the entire range of cell concentrations tested when the platelet containers are stored under an enriched oxyyen atmosphere.

What is claimed is:

1. A method comprising contacting a container holding about from $5 \times 10^8$ to $25 \times 10^8$ platelets/ml with an atmosphere having an oxygen proportion greater than about 21%, said container having a low oxygen transfer rate of about from 0.050 to 0.010 n moles/cm$^2$-min-cmHg.

2. The method of claim 1 wherein the oxygen proportion is greater than about 60%.

3. The method of claim 2 wherein the atmosphere is substantially 100% oxygen.

4. In a method for storing a composition containing about from $5 \times 10^8$ to $25 \times 10^8$ platelets/ml in a gas-permeable container having a low oxygen transfer rate of about from 0.050 to 0.010 n moles/cm$^2$-min-cmHg, the improvement comprising storing the container under an atmosphere having an oxygen proportion greater than about 21%.

5. In a method for storing a composition containing about from $5 \times 10^8$ to $25 \times 10^8$ platelets/ml in a container having an oxygen transfer rate of less than about 0.50 n moles/cm$^2$-min-cmHg, the improvement comprising exposing the container to an atmosphere having a proportion of oxygen greater than about 21%.

6. The method of claims 1 or 5 wherein the container is a polyvinyl chloride pouch.

7. The method of claim 6 wherein the polyvinyl chloride has a thickness greater than or equal to about 0.038 cm.

8. The method of claim 5 wherein the container is stored for up to 5 days.

9. In a method for storing a composition containing about from $5 \times 10^8$ to $25 \times 10^8$ platelets/ml in a plastic container formed from a film having an oxygen transfer rate of less than about 0.040 n moles/cm$^2$-min-cmHg, the improvement comprising continuously exposing the container to an atmosphere comprising at least about 60% oxygen, and agitating the container during such exposure.

10. The method of claim 9 wherein the proportion of carbon dioxide does not exceed about 5%.

11. A combination comprising:
(a) a gas-permeable container having a low oxygen transfer rate of about from 0.050 to 0.010 n moles/cm$^2$-min-cmHg, the container holding a composition containing about from $5 \times 10^8$ to $25 \times 10^8$ platelets/ml;
(b) a plenum surrounding at least a portion of the container;
(c) a source of gas having a proportion of oxygen greater than about 21% communicating with the plenum; and
(d) means for agitating the container.

12. A combination comprising:
(a) a gas-permeable container having a low oxygen transfer rate of about from 0.050 to 0.010 n moles/cm$^2$-min-cmHg, the container holding a composition containing about from $5 \times 10^8$ to $25 \times 10^8$ platelets/ml;
(b) a substantially gas impermeable plenum enclosing at least a portion of the container; and
(c) an atmosphere within the plenum in contact with the container which has a proportion of oxygen greater than about 21%.

13. The combination of claim 12 wherein the atmosphere is exchanged every 24 hours.

* * * * *